US 6,699,184 B2

(12) United States Patent
Felix et al.

(10) Patent No.: US 6,699,184 B2
(45) Date of Patent: Mar. 2, 2004

(54) FLUID MANAGEMENT ASSEMBLY HAVING A VENTED OUTLET LINE FOR USE IN ENDOSCOPIC PROCEDURES

(75) Inventors: Augustus Felix, Cranston, RI (US); Debra Ranucci, Smithfield, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 69 days.

(21) Appl. No.: 09/802,118

(22) Filed: Mar. 8, 2001

(65) Prior Publication Data

US 2001/0025160 A1 Sep. 27, 2001

Related U.S. Application Data

(63) Continuation-in-part of application No. 09/654,786, filed on Sep. 1, 2000, now Pat. No. 6,626,827.
(60) Provisional application No. 60/188,446, filed on Mar. 10, 2000.

(51) Int. Cl.[7] .......................... A61M 25/00; A61M 1/00
(52) U.S. Cl. ...................... 600/156; 604/324; 604/317; 604/284; 604/533
(58) Field of Search ................................ 600/156, 159, 600/158; 604/533, 538, 284, 324, 317, 905, 910, 911, 6.1, 326, 540, 541, 248, 10, 43, 506

(56) References Cited

U.S. PATENT DOCUMENTS

| | | | | | |
|---|---|---|---|---|---|
| 3,885,565 | A | * | 5/1975 | Satchell | 604/119 |
| 4,395,258 | A | * | 7/1983 | Wang et al. | 604/65 |
| 4,775,365 | A | * | 10/1988 | Swartz | 604/119 |
| 5,395,354 | A | * | 3/1995 | Vancaillie | 604/317 |
| 5,505,707 | A | * | 4/1996 | Manzie et al. | 604/131 |
| 5,599,333 | A | * | 2/1997 | Atkinson | 604/326 |
| 5,782,806 | A | * | 7/1998 | Knapp et al. | 604/131 |
| 6,102,889 | A | | 8/2000 | Wijnhoud | 604/80 |
| 6,149,633 | A | * | 11/2000 | Maaskamp | 604/317 |
| 6,282,442 | B1 | * | 8/2001 | DeStefano et al. | 604/21 |

* cited by examiner

Primary Examiner—John Mulcahy
Assistant Examiner—Jocelyn Ram
(74) Attorney, Agent, or Firm—Darby & Darby

(57) ABSTRACT

A system is provided for aspirating fluid from a surgical site. The system includes an outlet tube that leads to a suction canister or other suitable receptacle for collecting fluid. The outlet tube includes an anti-siphon adapter which defines an atmospheric vent downstream of the outflow connection to an endoscopic device. The vent allows atmospheric pressure to enter the outlet tube to increase the pressure at the outflow of the endoscopic device.

34 Claims, 9 Drawing Sheets

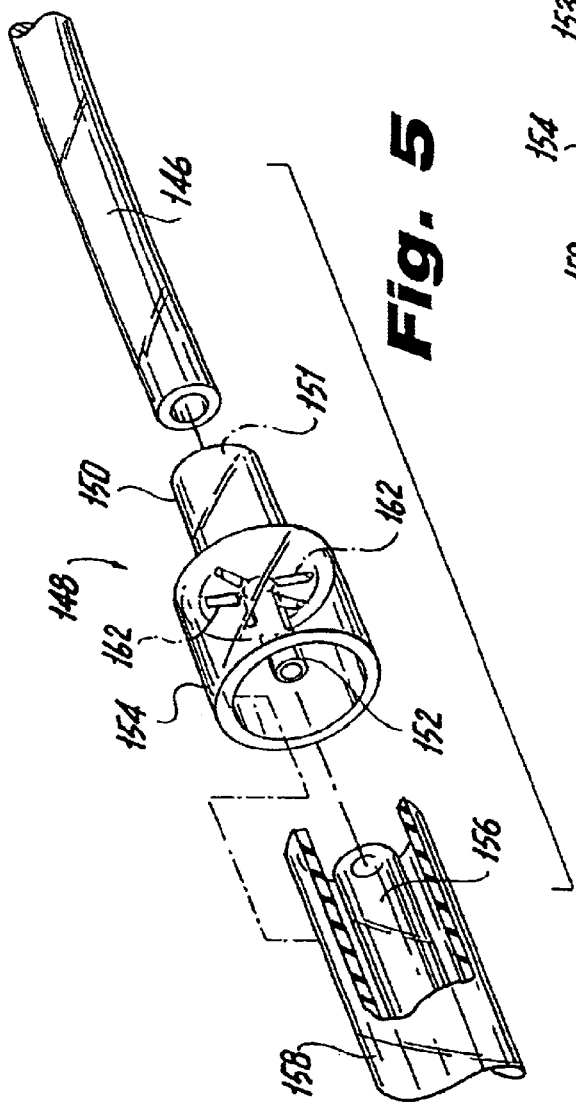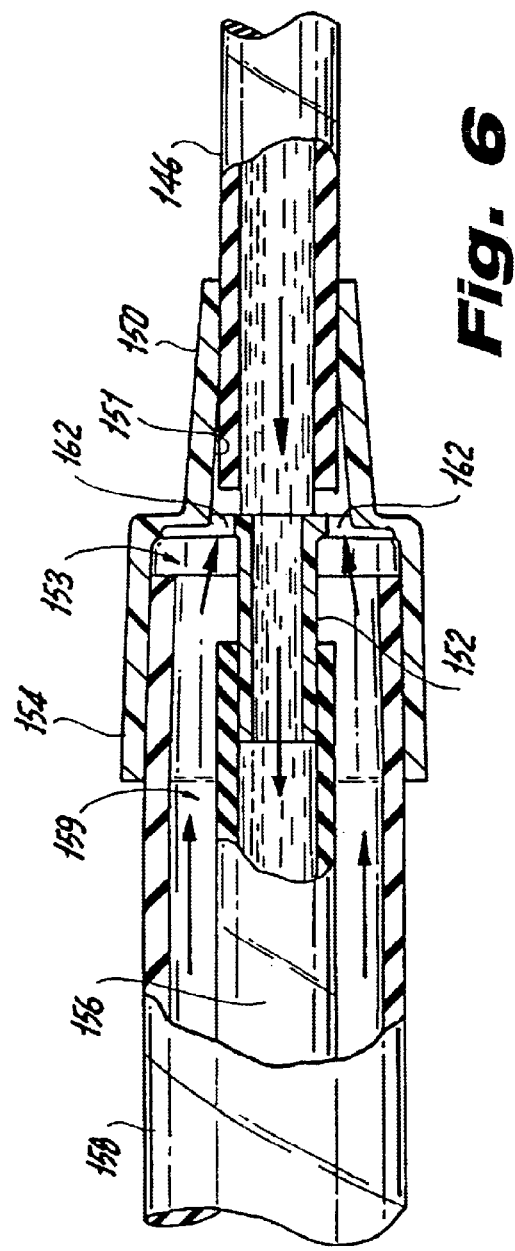

FLUID MANAGEMENT ASSEMBLY HAVING A VENTED OUTLET LINE FOR USE IN ENDOSCOPIC PROCEDURES

CROSS REFERENCE TO RELATED APPLICATIONS

This application is a continuation-in-part of U.S. patent application Ser. No. 09/654,786, filed Sep. 1, 2000, entitled "Fluid Management Assembly for Use in Endoscopic Procedures" (now U.S. Pat. No. 6,626,627) and this application claims the benefit of U.S. patent application Ser. No. 60/188,446, filed Mar. 10, 2000, entitled "Vented Outline Line for a Surgical Aspiration Device, and, both of which are hereby incorporated by reference in their entirety.

FIELD OF THE INVENTION

The present invention relates generally to fluid management systems and, more particularly, to an endoscopic distention fluid management assembly, having a vented outlet line, for use in an endoscopic procedure.

BACKGROUND OF THE INVENTION

Systems for distending and irrigating a surgical site during a surgical procedure, e.g., during a procedure to remove diseased tissue in the uterus, knee, shoulder, bladder and the like are well known in the art. A typical irrigation system includes a source of biocompatible fluid, e.g., a feed bag, tubing which delivers the fluid to the surgical site, and a pump which pumps fluid from the fluid source into the surgical site. The purpose of the irrigation system, at least in part, is to distend the operative space within the uterus, knee, shoulder, bladder, and the like, so that the clinician can clearly identify the anatomy and subsequently remove diseased tissue. A means for aspirating the fluid is typically also provided to remove fluid from the operative space, to flush out loose debris in order to maintain visibility of the surgical site for example, when the fluid becomes somewhat opaque and hard to see through. This type of system forms a part of an overall fluid management system or assembly which controls the flow of fluid.

Different surgical procedures require different irrigation parameters, e.g., fluid pressure and flow rate. Therefore, there are known irrigation systems in which the pressure and/or flow-rate of the irrigation fluid are controlled or varied to accommodate different surgical procedures. For example, U.S. Pat. No. 5,460,490 to Carr et al. describes an irrigation system which can be operated in a plurality of modes for different endoscopic surgical procedures, such as laparoscopic, arthroscopic or hysteroscopic procedures, the disclosure of which is hereby expressly incorporated by reference.

Typical aspiration systems include a suction canister which is attached to an outlet tube. The suction canister is operative to create a negative pressure in the outlet tube to remove fluid from the surgical site. In addition, such systems can be typically operated in a gravity flow mode, in which the fluid is aspirated under gravity and is simply collected and stored by the suction canister.

Such an arrangement can result in some negative performance characteristics. For example, in a gravity flow mode the fluid flows through a vertical length of tubing, which creates a siphon effect and therefore a negative pressure within the tube, which acts to reduce the positive pressure in the operative space, thereby reducing the amount of distention. Moreover, when suction is applied through the outlet tube, high levels of suction may be applied to the operative space, thereby also resulting in an unwanted reduction in the degree of distention within the operative space. This is an undesirable condition and can lead to operative complications.

Over the duration of the surgical procedure, an individual, such as a nurse, measures the amount of fluid being delivered to the patient and the amount of fluid which is recovered from the patient during the procedure. If the amount of fluid being recovered from the patient is less than the amount of fluid being delivered to the patient, a fluid deficit results. A fluid deficit may result due to any number of reasons including but not limited to the occurrence of fluid loss which results from leakage through a cervical seal as well as fluid loss through an outflow port of the endoscope. Since fluid monitoring is a very important part of managing the patient during the operative procedure, all fluids exiting the operative space (i.e., an organ or joint capsule) must be balanced with the fluids entering the operative space so as to maintain an account of the occurrence of any fluid deficit during the procedure. In addition, it is important to monitor whether a fluid imbalance occurs as a result of the patient absorbing an excessive quantity of fluid. If a patient absorbs an excessive quantity of fluid, complications can result including those of a serious nature. Therefore, it is important to continuously monitor the fluids in the operative space during the operative procedure to ensure that the uterus is properly distended to permit sufficient visualization thereof and to ensure that the patient's safety is maintained.

Typically, the clinician will use a fluid collection system as the surgical procedure is being performed so that fluid may be recovered and collected from the operative site. The endoscope contains an outflow port in which fluid is transferred from the operative site to a remote location where it is collected in a receptacle, such as the suction canister, and then measured to ascertain the total fluid loss of the patient during the procedure. During the procedure, a pouch drape or the like is typically used and is disposed underneath the patient. This drape is designed to collect any fluid which may be discharged from the patient during the procedure. The fluid is caught in the pouch portion and is collected therein for delivery to the remote collection receptacle (the suction canister). The drape and more specifically the pouch portion thereof is also likewise connected to the collection receptacle by means of a fluid carrying device such as attachable tubing which permits the fluid to be effectively transferred to the collection receptacle.

Now referring to FIG. 1 which illustrates a conventional fluid management assembly, generally designated at 10. The collection system 10 comprises a first fluid carrying member 12 which is connected at a first end 14 to a first connector 16 which is designed to engagingly mate with the outflow port of an endoscope (not shown). A second end 17 of the first fluid carrying member 12 is connected to a Y-connector 18 and more specifically is connected to a first leg 20 thereof. The management assembly 10 further includes a second fluid carrying member 22 which is coupled to a pouch drape (not shown) at a first end 24 thereof. The first end 24 preferably has a second connector 26 coupled thereto which is designed to permit attachment of the second fluid carrying member 22 to the pouch drape. A second end 28 of the second fluid carrying member 22 is connected to a second leg 30 of the Y-connector 18 with the first and second legs 20, 30 being in parallel orientation relative to one another.

The Y-connector 18 also includes a main leg 32 which extends in an opposite direction relative to the first and second legs 20, 30. The main leg 32 receives and is coupled to a main fluid carrying member 34 which receives fluid from both the first and second fluid carrying members 12, 22 and directs the fluid to a suction source (not shown). It will be appreciated that the suction source serves to supply a sufficient suction force so that the fluid is drawn through all the members 12, 22, 34 and is delivered to the collection receptacle (the suction source). Preferably, the first, second, and third fluid carrying members 12, 22, 34, respectively, comprise tubing which is suitable for use in the intended medical procedures described herein. At the end of the procedure, the total volume of the fluid collected in the collection receptacle is reconciled with the total input volume and a fluid deficit, if any, is calculated for the patient.

The management assembly 10 also preferably includes a pinch clamp 36 which is disposed about the first fluid carrying member 12 and is designed to selectively restrict the flow rate of fluid through the first carrying member 12. The illustrated pinch clamp 36 includes a ratchet mechanism which is designed to pinch the first fluid carrying member 12 between a pair of protuberances, generally indicated at 38. As the pinch clamp 36 is manipulated so that the first fluid carrying member 12 is further constricted between the protuberances 38, the flow rate of the fluid decreases.

The management assembly 10 also preferably further includes a flow restrictor (not shown) which is coupled to the first end 24 of the second fluid carrying member 22. The pouch drape does not always contain fluid and when this condition exists, the Y-connector 18 is vented to atmosphere which reduces the suction applied to the endoscope line (the first fluid carrying member 12). By being inserted into the second fluid carrying member 22, the flow restrictor 39 is designed to enhance the suction in the endoscope line so that the fluid is properly drawn from the endoscope whether or not fluid is present in the drape.

While suitable for its intended purpose, the above-described conventional management assembly 10 has associated disadvantages which results in reduced distention at the operative site. Because distention is dependent upon on both inflow and outflow performance, optimization of the fluid inflow and outflow will result in distention being likewise optimized. During distention of the operative space, fluid is pumped into the operative space to develop positive pressure, which is required in order to increase the volume of the operative space. The fluid pumped into the uterine space is delivered by means of the endoscope which has an inflow port along with the aforementioned outflow port. Fluid which enters the operative space through the inflow port is then relieved through the outflow port. When the fluid is relieved through the outflow port, it is permitted to flow under gravity into the pouch drape for subsequent aspiration into the collection receptacle.

During gravity flow from the outflow port, the fluid flows through a vertical length of the first fluid carrying member 12 which creates the siphon effect previously-mentioned. The magnitude of the siphon effect will depend upon the length of the first fluid carrying member 12 which hangs vertically below the patient. This siphon effect acts as a negative pressure source which serves to reduce the positive pressure acting within the operative space and hence, reduces the amount of distention. This reduction in distention, if significant enough, can slow down the surgical procedure and result in an increase in bleeding which in turn results in impaired visualization of the anatomy.

In addition, the Y-connector 18, as previously described, serves to receive both the fluids from the first and second fluid carrying members 12, 22 under suction so that all of the patient's fluids may be pooled into one collection canister (the collection receptacle). Using a Y-connector arrangement can result in a decrease in performance since the system flow needs to be mechanically balanced to allow adequate simultaneous entrainment from both the first and second legs 20, 30 of the Y-connector 18. If the first and second legs 20, 30 are not balanced, flow may be biased to one of the first and second legs 20, 30 because the fluid seals the leg with less resistance causing a sumping action to occur. The occurrence of a sumping action results in cycling of pressures at the operative site, bleeding and increases surgical procedure time. For example, when there is a fluid build-up in the pouch drape, the drape acts as a reservoir creating a column of fluid in the second fluid carrying member 22. Because of the column of fluid, the pressure in the second fluid carrying member 22 is increased and this may create a fluid seal which limits the fluid flow through the first fluid carrying member 12 (endoscope line). This causes a recycling of the pressure at the operative site which is undesirable.

Accordingly, it will be apparent to those skilled in the art that there continues to be a need for an improved fluid management system for use in various surgical procedures. The present invention addresses that need.

SUMMARY OF THE INVENTION

In one aspect of the present invention, a fluid management assembly for use in an endoscopic procedure is provided. The assembly comprises a first line defining a passage for the flow of fluid with the first line having a first end for connection to an endoscope and an opposing second end. A second line defining a passage for the flow of fluid is also provided with the second line having a first end for connection to a drape and an opposing second end. The assembly further includes a Y-connector having first and second legs in fluid communication with the second ends of the first and second lines. A third line is coupled at a first end to a third leg of the Y-connector and the third line has a second end for connection to a suction source. The third line has a predetermined length such that the Y-connector is positioned in close proximate relation to the suction source, wherein the length of the third line is less than the length of the first and second lines.

The assembly also includes an atmospheric vent disposed within the first line for introducing atmospheric pressure into the first line to relieve any excessive negative pressure build-up within the first line. The atmospheric vent causes a reduction in the negative pressure within the first line when it is open by introducing atmospheric pressure into the first line. Depending upon the embodiment, the atmospheric vent may be either biased open so that the it closes only when a positive pressure build-up is observed in the first line or it may be normally biased closed so that it opens when a set point (pressure value) of the vent is exceeded.

In another aspect of the present invention, a system is provided which includes an outlet tube that leads to a suction canister or other suitable receptacle for collecting fluid. The outlet tube includes an anti-siphon adapter which defines an atmospheric vent downstream of an endoscope or other similar surgical device. The vent allows atmospheric pressure to enter the outflow tube to increase the pressure at the outflow of the endoscope, thereby substantially preventing a siphoning effect from occurring within the outlet tube.

BRIEF DESCRIPTION OF THE DRAWINGS

The present invention will be understood and appreciated more fully from the following detailed description of an illustrative embodiment of the invention, taken in conjunction with the accompanying drawings, in which:

FIG. 5 is an exploded, perspective view of an anti-siphon adapter and tubing included in the outlet tube assembly of FIG. 4;

FIG. 6 is a cross-sectional side view of a portion of the outlet tube and adapter of FIG. 5;

DETAILED DESCRIPTION OF THE PREFERRED EMBODIMENT

Figure 2:
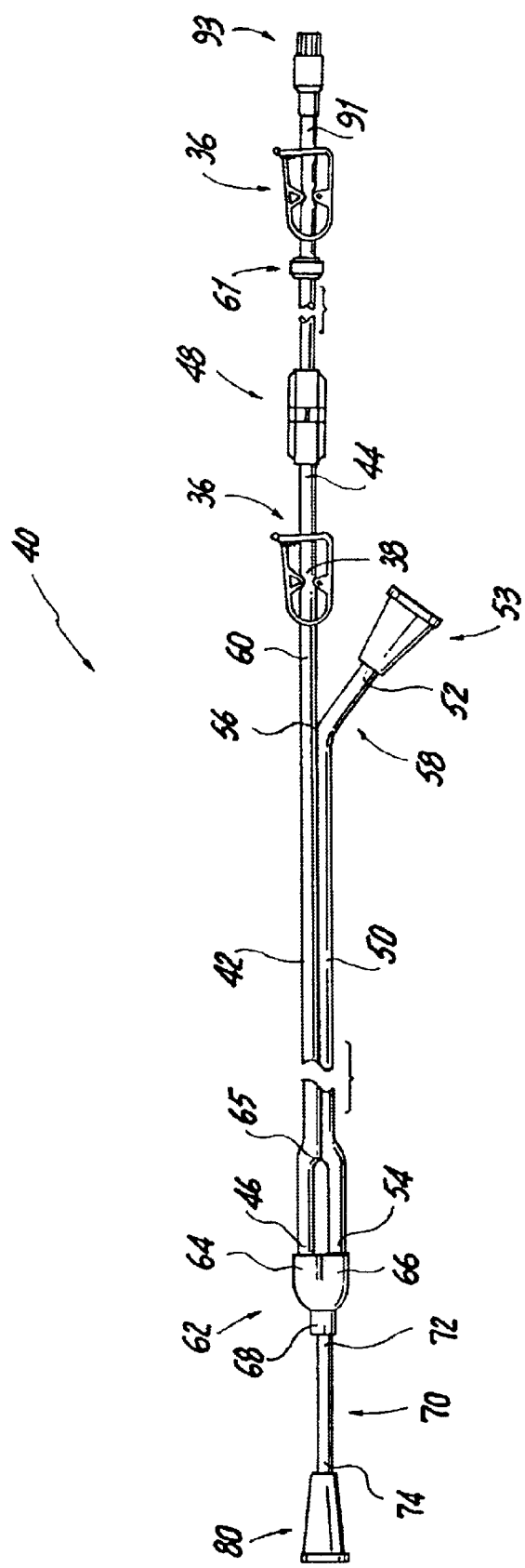
FIG. 2 is a side elevational view of a fluid management assembly according to an exemplary embodiment of the present invention.
Figure 3:
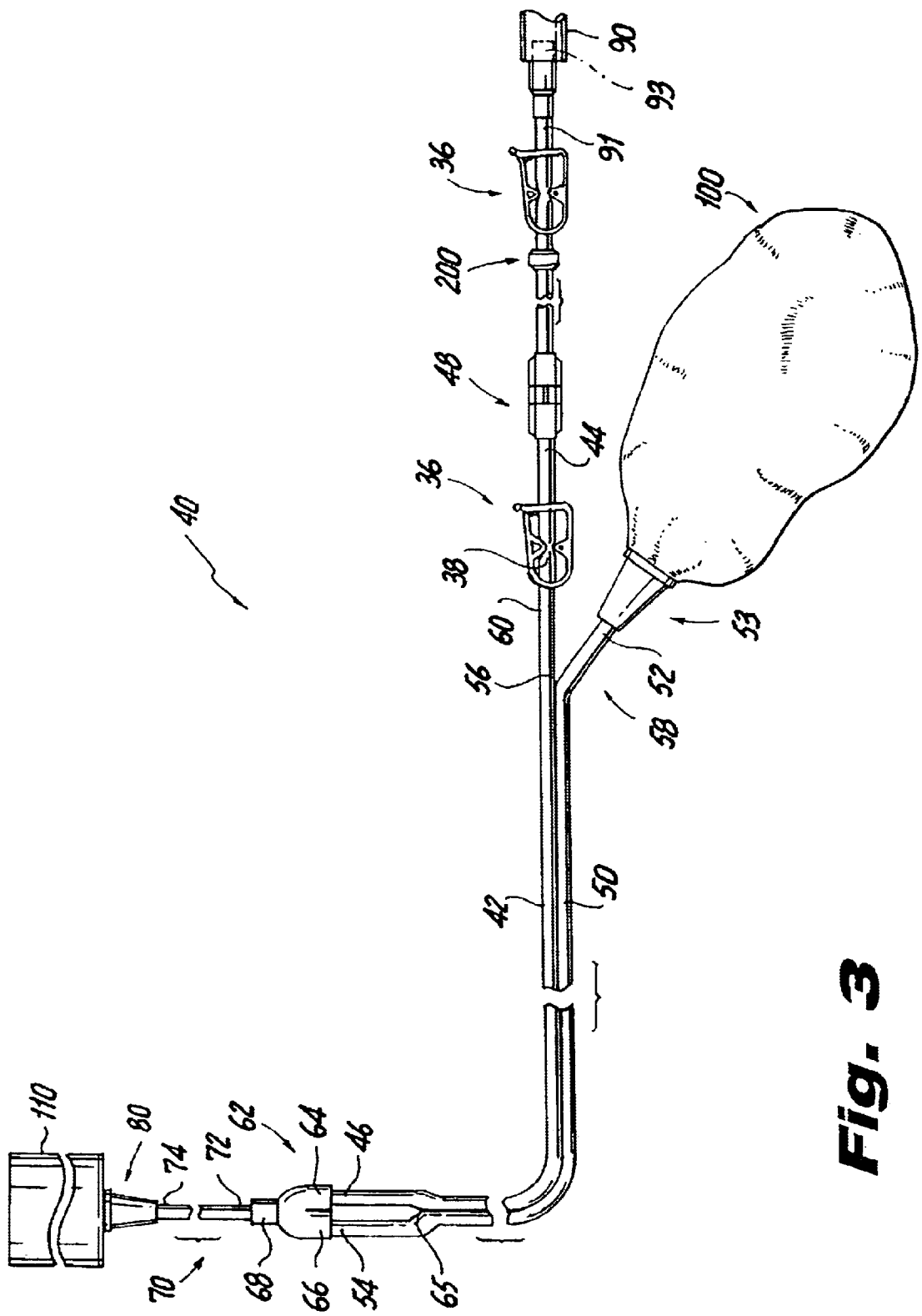
FIG. 3 is a side elevational view of the fluid management assembly of FIG. 2 shown in use with conventional surgical equipment during an operative procedure.

Referring to FIGS. 2 and 3, a fluid management assembly is presented and is generally indicated at 40. FIG. 3 illustrates the fluid management assembly 40 in use according to the present invention with conventional accessory equipment during a typical endoscopic procedure, as will be described in greater detail hereinafter. The fluid management assembly 40 may be referred to as having a dual lumen design and comprises a first fluid carrying member 42 and a second fluid carrying member 50. The first fluid carrying member 42 has a first end 44 and an opposing second end 46. The first end 44 preferably connects to a first connector 48 which is designed to fluidly mate with outflow tubing 91 which includes a connector 93 at one end for mating with an endoscope 90 (e.g., hysteroscope). One type of suitable connector 48 is a large bore Quosina connector which is presented in the sterile field in a capped state. More specifically, the first connector 48 provides fluid communication between an outflow port (not shown) of the endoscope 90 and the first fluid carrying member 42 through the outflow tubing 91.

The second fluid carrying member 50 includes a first end 52 and an opposing second end 54 with the second ends 46, 54 of the first and second fluid carrying members 42, 50, respectively, being positioned proximate one another. The first end 52 is coupled to a pouch drape 100 (e.g., hysteroscope pouch drape) by means of a second connector 53 so that fluid communication is provided between the hysteroscope pouch drape 100 and the second fluid carrying member 50 for drainage of fluid build-up within the drape 100 during the surgical procedure. One suitable type of second connector 53 is a suction connector for fluidly connecting the drape 100 to the assembly 40.

In the illustrated embodiment, each of the first and second fluid carrying members 42, 50 comprises a predetermined length of tubing material. The first and second fluid carrying members 42, 50 are preferably co-joined (affixed) along at least a portion of each of their lengths. For the purpose of illustration and according to one exemplary embodiment, the first and second fluid carrying members 42, 50 are co-joined for a length of approximately 10 feet and separate at a first location 56 to form a drape leg 58 and a suction outflow leg 60. It will be appreciated that the drape leg 58 comprises a length of the second fluid carrying member 50 extending from the first location 56 to the first end 52. The suction outflow leg 60 comprises a length of the first fluid carrying member 42 extending from the first location 56 to the first end 44. In the exemplary embodiment, the drape leg 58 has a length of approximately 10 inches and the suction outflow leg 60 has a length of about 20 inches. The suction outflow leg 60 is thus attached to the outflow tubing 91 at the connector 48. The outflow tubing 91 extends from the connector 48 to the endoscope 90 (e.g., hysteroscope) and serves to transfer fluid from the outflow port of the endoscope 90 to the suction outflow leg 60.

In a similar manner, the co-joined first and second fluid carrying members 42, 50 separate at a second location 65 which is distal to the first location 56. The separation at the second location 65 causes the first and second fluid carrying members 42, 50 to be spaced from one another for a predetermined length so that each of the members 42, 50 may be grasped and manipulated as will be described in greater detail hereinafter.

Preferably, the outflow tubing 91 is provided with an atmospheric vent 200 which is disposed proximate to the connector end 93 and thus proximate to the endoscope 90. The atmospheric vent will be described in greater detail with reference to additional FIGS. In the exemplary embodiment, the atmospheric vent 200 is formed approximately 6 inches from the outflow connection of the endoscope 90 (at the connector end 93). The atmospheric vent 200 permits atmospheric pressure to enter the outflow port of the endoscope 90 and this results in a pressure increase at the outflow port. Other features of the atmospheric vent 200 will be described hereinafter when the operation of assembly 40 is described in greater detail.

The fluid management assembly 40 further includes a Y-connector which is generally indicated at 62. The Y-connector 62 is formed of first and second spaced legs 64, 66, respectively, which converge to a main leg 68 which extends in a direction away from the first and second spaced legs 64, 66. The first leg 64 mates with and is secured to the second end 46 of the first fluid carrying member 42 and the second leg 66 mates with and is secured to the second end 54 of the second fluid carrying member 50. Thus, the first leg 64 serves to receive the fluid flowing through the first fluid carrying member 42 from the endoscope 90 and the second leg 66 serves to receive the fluid flowing through the second fluid carrying member 50.

The Y-connector 62 acts to mix and direct the fluids from the independent fluid conduits (members 42, 50) to a suction conduit, generally indicated at 70. The main leg 68 of the Y-connector 62 is coupled to the suction conduit 70 so that fluid communication is established therebetween. More specifically, the suction conduit 70 is connected at a first end 72 to the Y-connector 62 and connects at a second end 74 to a suction source 110 by means of an adapter 80 which is designed to provide a secure attachment between the suction source 110 and the assembly 40 and provide fluid communication therebetween. It will be appreciated that the suction source 110 provides a suction force throughout the system and also serves as a collection receptacle for receiving fluids from both the outflow port of the endoscope 90 and the pouch drape 100. In one exemplary embodiment, the suction source 110 comprises a suction cannister and the suction conduit 70 comprises a predetermined length of tubing. A suitable suction cannister 110 is commercially available from a number of manufacturers, including Bemis, Baxter, and Abbott Laboratories. According to one exemplary embodiment of the present invention, the suction conduit 70 has a length of approximately 6 inches.

The fluid management assembly 40 typically will also include the pinch clamp 36 which is disposed about the first fluid carrying member 42 for selectively restricting the flow of fluid within the first fluid carrying member 42. Any number of suitable pinch clamps 36 may be used with assembly 40. The illustrated pinch clamp 36 has a ratchet mechanism that selectively pinches the first fluid carrying member 42. The first fluid carrying member 42 is disposed between the pair of protuberances 38 and as the ratchet mechanism is actuated, the distance between the protuberances 38 either decreases resulting in the first fluid carrying member 42 being increasingly pinched causing an increased restriction in the fluid flow through member 42 or the distance decreases resulting in an increase in fluid flow through the first fluid carrying member 42. In the illustrated embodiment, two pinch clamps 36 are shown, one being disposed about the suction outflow leg 60 and the other disposed about the outflow tubing 91. It will be understood that the precise location of the pinch clamps 36 is not critical and depending upon a number of factors, the pinch clamps 36 may be positioned at a variety of locations along the first fluid carrying member 42.

According to the present invention, it has been discovered that the repositioning of the Y-connector 62 yields several key benefits which result in improved distention of the uterus during the surgical procedure. More specifically, the distance between the Y-connector 62 and the suction source 110 is significantly reduced as it has been discovered that improved performance is realized by relocating the Y-connector 62 to a more proximate position relative to the suction source 110. The assembly 40 according to the present invention provides constant flow to the endoscope 90 and to the hysteroscope pouch drape 100 by elongating the legs of the Y-tubing set in order to minimize mixing and dependency. In other words, the length of each of the drape leg 58 and the suction outflow leg 60 is increased and represent independent fluid conduits which extend separately from the sterile field before combining at the Y-connector 62. By repositioning the Y-connector 62 closer to the suction source 110, the Y-connector 62 and the fluid traveling therethrough are exposed to greater suction forces because the Y-connector 62 is located in a more downstream location relative to the suction source 110 and thus the suction forces acting on the Y-connector 62 are greater and the influence of any variances in fluid between the endoscope line and the drape line are minimized. In the illustrated embodiment, the distance between the Y-connector 62 and the suction source 110 is less than about one foot and preferably is approximately 6 inches. Conventionally, the Y-connector is connected to a conduit (main fluid carrying member 34) having a length of about 108 inches and the fluid was to travel this distance before being deposited into the collecting receptacle (suction canister 110). It will be understood that the aforementioned lengths are merely illustrative and of an exemplary nature and do not limit the scope of the present invention.

Figure 1:
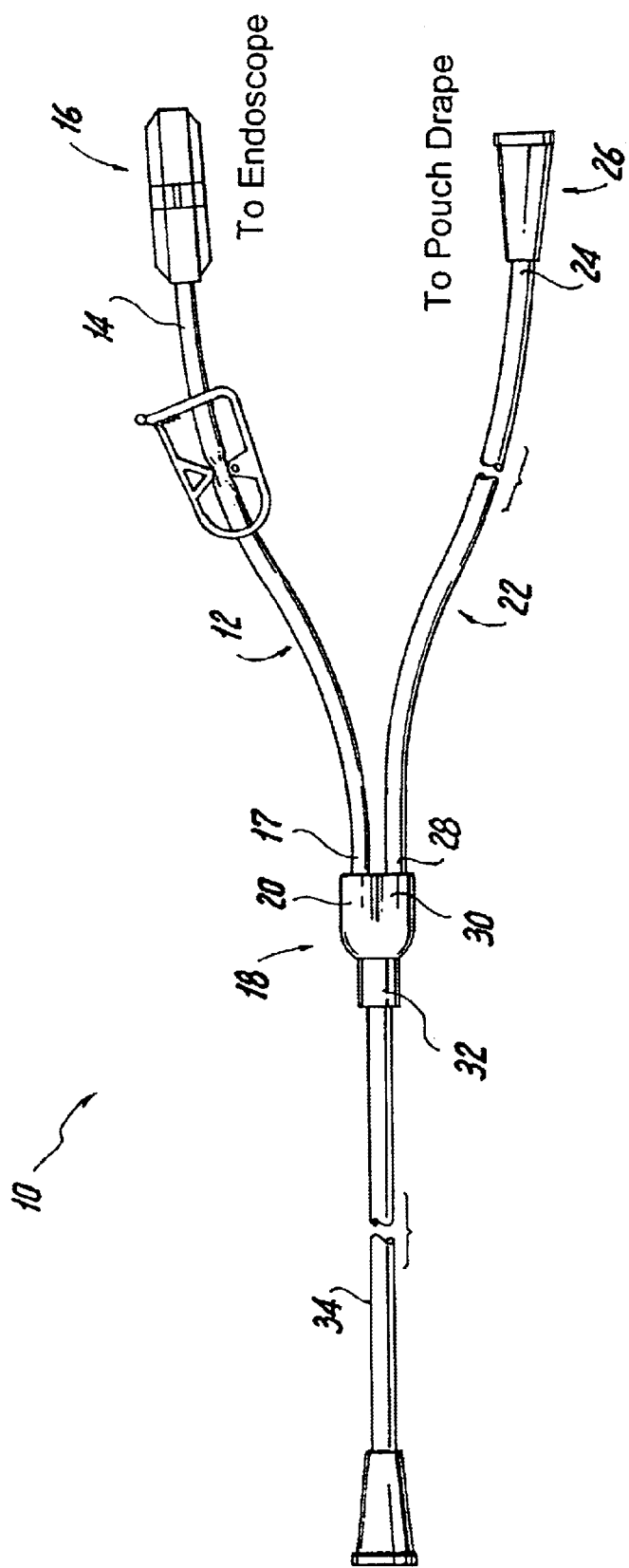
FIG. 1 is a side elevational view of a conventional fluid management assembly for use in an endoscopic surgical procedure.

Referring now to FIGS. 1–3. Advantageously, the repositioning of the Y-connector 62 in the present assembly 40 eliminates the disadvantages which were associated with fluid pooling within the Y-connector 18 of the conventional assembly 10. In the conventional assembly 10, the Y-connector 18 drapes downwardly from the pouch drape and the endoscope and ultimately becomes saturated with fluid as the fluid collects or pools in the Y-connector 18 as the fluid flows downwardly into the Y-connector 18. In such an assembly 10 which is open to atmosphere, the fluid wants to seek its own level and hence the fluid collected in the pouch drape wants to flow upwardly into the leg of tubing which leads to the endoscope. This reflux action prevents fluid from exiting the outflow port of the endoscope and hence inhibits fluid turnover in the operative space, i.e., uterus, knee, etc.

By positioning the Y-connector 62 in a more downstream location closer to the suction source 110 itself, the pooling of fluid within the Y-connector body is eliminated since the fluid is entrained upwardly into the Y-connector 62. More specifically, the suction source 110 is positioned at least above the level of the first and second fluid carrying members 42, 50, respectively, and also preferably above the level of the pouch drape 100. This results in the fluid being entrained upwardly into the Y-connector 62 during operation. This is in contrast to the previous assembly 10 in which the fluid is entrained downwardly into the Y-connector and thus tends to pool therein resulting in a liquid seal being formed. As previously described, the presence of a liquid seal results in sumping action. The Y-connector leg, having the lesser resistance, is effectively sealed which results in cycling of pressures at the operative site, bleeding and an overall increase in the surgical procedure time. By virtue of repositioning of the Y-connector 62 in the present assembly 40, the first and second legs 64, 66 of the Y-connector 62 are exposed to lower negative pressures and, in combination with the fact that the Y-connector 62 is exposed to greater suction forces due to its repositioning, the overall performance of the assembly 40 is significantly increased in comparison to the prior mechanical restrictor assembly 10.

The assembly 40 has an anti-siphon conduit arrangement provided for use on the outflow port of the endoscope 90. This arrangement relieves negative pressures associated with the vertical positioning of the outflow conduit member (first fluid carrying member 42) relative to the operative space. The present assembly 40 also reduces negative pressure applied to uterus when suction is attached directly to the outflow port of the endoscope 90. Furthermore, the atmospheric vent 200 provided in the outflow tubing 91 (scope line) provides suction relief during the surgical procedure.

By increasing the length of the drape leg 58 and the suction outflow leg 60 and maintaining the same or similar inner diameters thereof, the flow/pressure within each leg 58, 60 is essentially the same; however, the first and second fluid carrying members 42, 50 engage the Y-connector 62 further downstream where the suction forces are greater. The inverted positioning of the Y-connector 62 in this downstream location results in the resistance from the fluid in either leg 58, 60 being minimized. Because of the substantial length of the drape and suction outflow legs 58, 60 prior to their connection to the Y-connector 62, it is not necessary to restrict flow in the second fluid carrying member 50 (drape line) to provide adequate suction on the endoscope 90 when the drape 100 is empty. In one exemplary embodiment, the inner diameter of the suction outflow leg 60 is about 0.190 inches and the inner diameter of the drape leg 58 is 0.125 inches.

Thus, the present invention eliminates the need for using a flow restrictor with the endoscopic line and this generally reduces the cost of the surgical procedure and the complexity thereof. Furthermore, the accumulated fluid collected within the drape 100 is unlikely to create a fluid seal which would restrict flow from the endoscope 90 when the present assembly 40 is used. Accordingly, pressure fluctuations in the uterus are eliminated and flow is enhanced when fluid is aspirated simultaneously from the drape 100 and the endoscope 90. Using the dual lumen suction design of the present assembly 40 of the present invention, the pressure inside of the uterus is not changed based upon the method of fluid outflow. In other words, the pressure does not change whether the fluid flows by gravity or by means of suction assist. Furthermore, the pressure inside of the uterus is not affected by the presence of fluid in the drape 100 during suction assisted outflow of the fluid.

Another consideration in optimizing the level of distention is the rate of which the fluid is being pulled from the uterus. The fluid flow rate is important for visualization purposes (i.e. to minimize white and red outs). This fluid flow rate is a function of airflow rate at the first end of the endoscopic line that is connected to the outflow port of the endoscope. The dual lumen design of the present invention yields equal airflow rates at the points of connection between the endoscopic line and the outflow port of the endoscope 90 and the drape line and the drape 100 and the present design further eliminates the fluctuation of airflow through the endoscopic line when fluid is present in the drape 100. The airflow rate through the endoscopic line is not reduced when fluid is present in the drape. This results in improved pressure balance and thus distention and visualization are likewise improved at the operative site.

Another advantage of the present invention is that the use of co-joined tubing in the assembly 40 gives the surgeon flexibility in selecting the length for the drape and suction outflow legs 58, 60. This permits the surgeon to custom tailor the length of either of legs 58, 60. For example, if the surgeon prefers to increase the length of the suction outflow leg 60, the surgeon may simply pull the legs 58, 60 apart from one another to further separate the two from one another and thereby increase the length of the leg portions 58, 60. This permits the surgeon greater latitude in using the assembly 40 with a number of types of medical equipment and the precise location of the equipment is not critical since the length of the leg portions 58, 60 may be customized to permit the assembly 40 to be effectively hooked-up to all of the requisite equipment.

Figure 4:
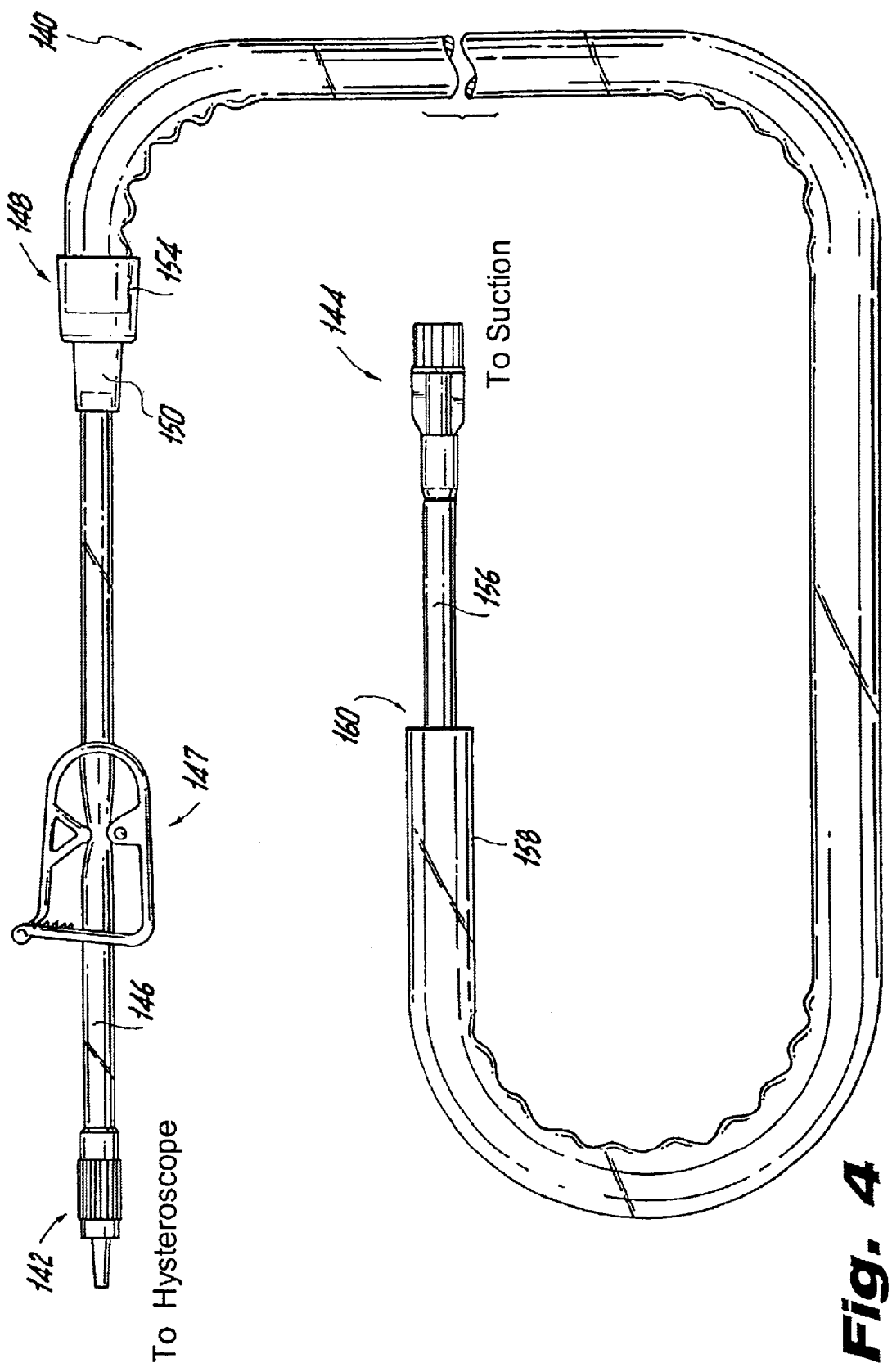
FIG. 4 is a side elevational view of one exemplary outlet tube assembly for use with the fluid management assembly of FIG. 2.

Reference is now made to FIG. 4 which schematically illustrates a side elevational view of an outlet tube 140 according to the present invention, which is designed for use with the fluid management assembly 40, shown in FIGS. 2–3, or a similar type assembly. With reference to FIGS. 2–3, the outlet tube 140 takes the place of the outflow tubing 91 when incorporated into the assembly 40. The fluid management assembly 40, in one illustrative embodiment, includes an endoscope, such as a hysteroscope. As is known in the art, the endoscope typically includes both inflow and outflow ports (or valves). Fluid is delivered to a surgical site (the "operative space") through a delivery tube connected to the inflow port, which serves to distend the operative space. Fluid in the operative space is then relieved through the outflow port to an outlet line, such as the outlet tube 140 of the present invention. The outlet tube 140 includes a suitable connector 142, for example, a leer fitting, disposed at one end of the tube 140 to connect to the outflow port. The outlet tube 140 also includes a suitable connector 144, such as an internally threaded cap with a through lumen, at the opposite end of the tube 140 to connect to a port of the suction canister (not shown) or other suitable fluid receptacle to deliver fluid to the canister. The outlet tube 140 also preferably includes a conventional tube clamp 147 which, as is well known in the art, may be used to selectively close the flow path through the outlet tube 140.

When the fluid enters the outlet tube 140, it may flow under gravity to the suction canister, or alternatively the suction canister may be actuated to apply a negative pressure to the outflow port of the hysteroscope through the outlet tube 140 to withdraw fluid from the operative space. In either event, the outlet tube 140 of the present invention improves the performance of the irrigation system, as is now described in detail.

Referring now to FIGS. 4–6, the outlet tube 140 includes the connector 142, which is permanently connected to a length of tubing 146. Thus, when the connector 142 is releasably connected to the outflow port of the hysteroscope or other device, fluid will flow through an interior lumen of the connector and into the length of tubing 146. The length of tubing 146 leads to an adapter member 148 (FIG. 5) which acts as the atmospheric vent 200 shown in the assembly 40 of FIGS. 2–3. In other words, the atmospheric vent 200 may comprise the adapter member 148 in one embodiment.

The adapter member 148 includes an inlet nipple region 150 telescopically extended over the length of tubing 146 for fluid communication therebetween (FIG. 6). The nipple region 150 defines an interior cavity 151 which receives the fluid from the length of tubing 146.

The adapter member 148 further includes an internal structure 153 that defines a pair of coaxial, generally tubular members 152 and 154. The inner member 152 connects to a tube segment 156 which leads to the suction canister and includes the connector 144 at the distal end thereof. The outer member 154 connects to a concentric sleeve member 158 which preferably extends over a substantial length of the tube segment 156 and includes a free distal end 160 which opens to atmosphere. The sleeve 158 and tube segment 156 define an annular space 159 between the two, the function of which is described in more detail below. One or more openings 162 are formed inside of the adapter member 148 to permit flow from the outer member 154 to the interior cavity 151. Thus, air from the atmosphere may be conducted through the space 159 defined between sleeve member 158 and tube segment 156 and into the interior cavity 151 of the adapter member 148. In this manner, the adapter member 148 prevents any vacuum effect from occurring within the outlet tube 140, such that siphoning does not occur because atmospheric air is continuously introduced into the fluid flowing from the tubing 146 to the tube segment 156.

By including the relatively long sleeve member 158 extending from the adapter member 148, a tortuous path is established to substantially prevent fluid leakage through the adapter member 148. In addition, due to the overlap of the tubing with the adapter member 148 and the negative pressure within the tube 156, the path through the tube 156 is the path of least resistance for the fluid being withdrawn, thereby making the path through the annular space 159 a relatively tortuous one. Thus, during normal conditions fluid will flow from the tubing 146 and into the inner member 152 and on through the tube 156, without flowing into the annular space between the sleeve 158 and tube 156. If the tube 156 clogs, then fluid may flow out through that annular space 159 because the path through the inner member 152 and tube 156 is no longer the path of least resistance. Instead, the path of least resistance is through the openings 162 and the space 159.

The adapter member 148 is preferably located as close to the outflow port of the endoscope or other device as is practical. In one embodiment, the adapter member 148 is located approximately six (6) inches from the outflow port, which leaves room for a clinician's hands to maneuver to outlet tube 140.

While one form of adapter member 148 has been shown and described, it will be apparent to those skilled in the art that other forms may be employed. For example, a hydrophobic vent can be incorporated into the adapter member 148. Also, a hydrophilic vent that closes when wet could be used in the adapter member 148. Alternatively, the adapter member 148 can incorporate a valve vent that is pre-loaded with some force to only open at certain levels of vacuum, such as a duckbill valve, an umbrella valve, or a spring-loaded valve.

It will be apparent that the openings 162 in the adapter member 148 provide a two-way path for fluid flow. Typically, when a negative pressure exists within the outlet tube 140, air is entrained via the annular space 159 between the sleeve 158 and tube 156. However, when the tube 156 is blocked, fluid builds up in the outlet tube 140 and flows out through the openings 162 and through the annular space 159 between the sleeve 158 and tube 156 when fluid is unable to flow through the tube 156.

In use, a clinician connects the connector 142 to the outflow port of the endoscope or other surgical device, and connects the connector 144 to the suction canister or other storage container. The clinician operates the endoscope to deliver fluid to the operative space in order to distend the space. At some point, the outflow port is opened, and fluid flows through the outlet tube 140 to the suction canister. The sleeve member 158 delivers atmospheric air to the adapter member 148 to prevent a siphoning effect from occurring within the outlet tube 140, so that the quantity of fluid withdrawn from the operative space can be controlled. Adapter member 148 thus acts as an anti-siphon device which breaks the suction and prevents any siphon action from occurring by introducing atmospheric air into the outlet tube 140 and more specifically, atmospheric air is introduced into the fluid flowing from the tube 146 to the tube 156.

While the outlet tube 140 of the present invention has been described in connection with an endoscopic procedure, it will be apparent to those skilled in the art that the outlet tube 140 may be used in connection with all closed cavity distention procedures. For example, the outlet tube 140 may be used in arthroscopic, cystoscopic, and other such procedures, in which a fluid is used to distend an operative space.

From the foregoing, it will be apparent to those skilled in the art that the present invention provides an improved outlet tube 140 for use in a surgical irrigation/aspiration system such as the fluid management assembly 40. The outlet tube 140 is designed to prevent siphoning, while minimizing or preventing leakage.

Referring now to FIGS. 7–10, in another embodiment of the present invention, the atmospheric vent 200 (FIG. 3) comprises a valve assembly 201, for use with an outlet tube 210. Outlet tube 210 is of a type which may be used with an irrigation system (not shown), such as the fluid management assembly 40 of FIGS. 2–3. When outlet tube 210 is used with the fluid management assembly 40, it takes the place of the outflow tube 91. The irrigation system may be any number of irrigation systems in which a fluid is delivered to an operative site for causing distention thereof and then the fluid is removed from the operative site. For example, the valve assembly 201 and outlet tube 210 may be associated with an endoscopic device. Endoscopic devices are used in a number of types of procedures, including but not limited to orthopedic procedures and hysteroscopic procedures.

More specifically, in one embodiment, the endoscopic device is a hysteroscope that includes both inflow and outflow ports (or valves). Fluid is delivered to a surgical site (the "operative space") through a delivery tube connected to the inflow port, which serves to distend the operative space. Fluid in the operative space is then relieved through the outflow port to an outlet line, such as the outflow tube 210 of the present invention. In another embodiment, the endoscope is an arthroscopic device for use in an arthroscopic procedure on a closed cavity, such as a knee, shoulder, ankle, wrist, etc. In other words, the valve assembly 201 and the outlet tube 210 are suitable for use in a wide range of irrigation systems and procedures where fluid distention occurs at the surgical site.

The outlet tube 210 includes a suitable connector 212, for example, a leer fitting, disposed at one end of the outlet tube 210 to connect to the outflow port of the device. The outlet tube 210 also includes a suitable connector 214, such as an internally threaded cap with a through lumen, at the opposite end of the outlet tube 210 to connect to a port of a suction cannister (not shown) or other suitable fluid receptacle. The outlet tube 210 thus delivers the fluid to the canister or other receptacle. The outlet tube 210 optionally may include a conventional tube clamp 220 which may be used to selectively occlude the outlet tube 210 to prevent fluid from flowing therethrough.

When the fluid enters the outlet tube 210, the fluid may flow under gravity to the suction canister (or other receptacle), or alternatively, a suction source associated with the suction canister may be actuated to apply a negative pressure to the outflow port of the endoscopic device through the outlet tube 210 to withdraw fluid from the operative space to the suction canister. During an endoscopic procedure, the fluid is delivered to the surgical site under pressure by any number of means, including using a pump. The fluid is therefore pumped at some positive pressure and the existence of this positive pressure causes distention at the surgical site. The negative pressure applied by the suction source serves to counter this positive pressure so that the surgical site does not become over-distended. Conversely, if the negative pressure applied by the suction canister exceeds the positive pressure of the system, excess negative pressure will result in the system. This is also an unfavorable condition as it results in distention loss, which causes loss of operative space, poor visualization, and in the case of arthroscopy, causes bleeding if a turniquet or the like is not used. Bleeding will result because the blood pressure will be higher than the fluid pressure in the operative site, e.g., a knee. In either event, the outlet tube 210 of the present invention improves the performance of the irrigation system as will now be described in greater detail.

Figure 7:
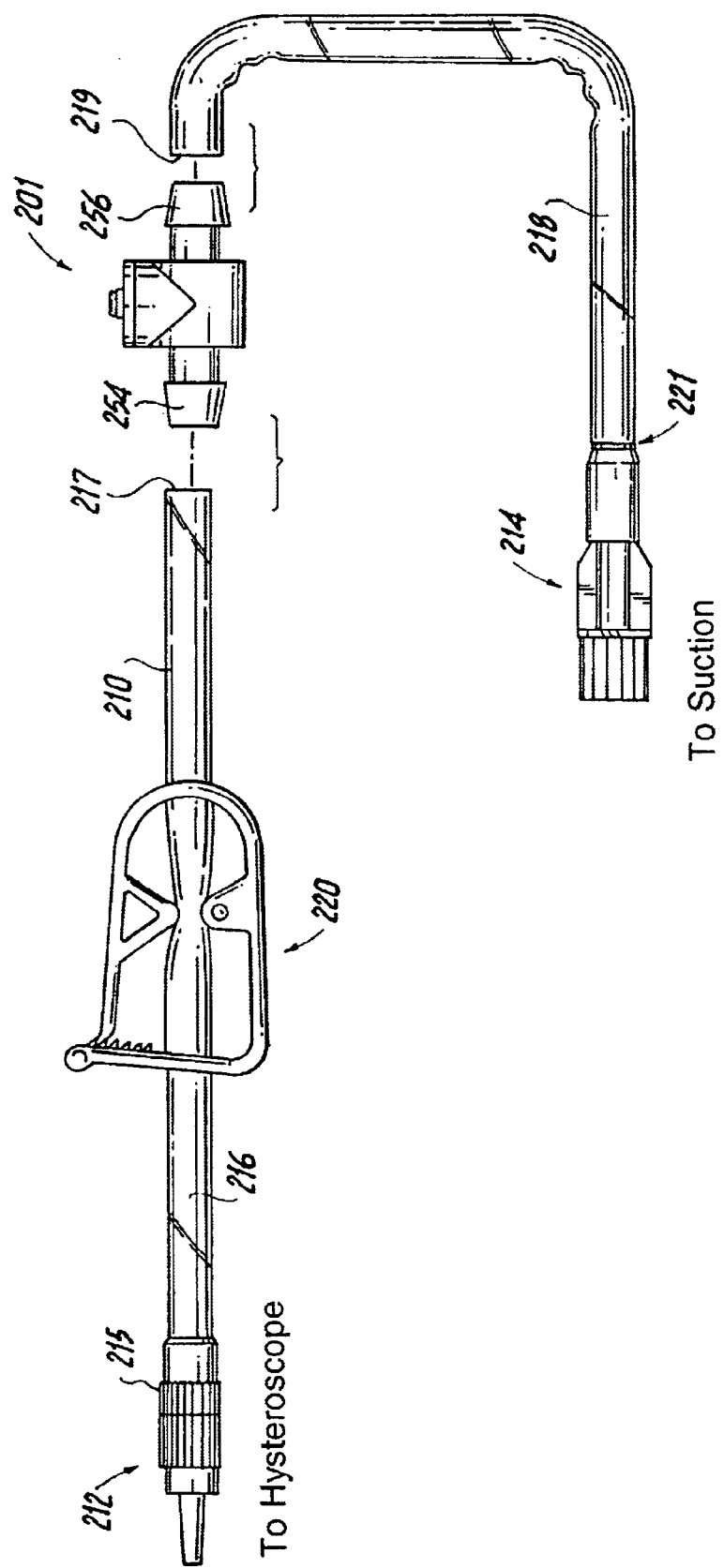
FIG. 7 is a side elevational view of one exemplary outlet tube assembly and a valve assembly according to one embodiment of the present invention.
Figure 8:
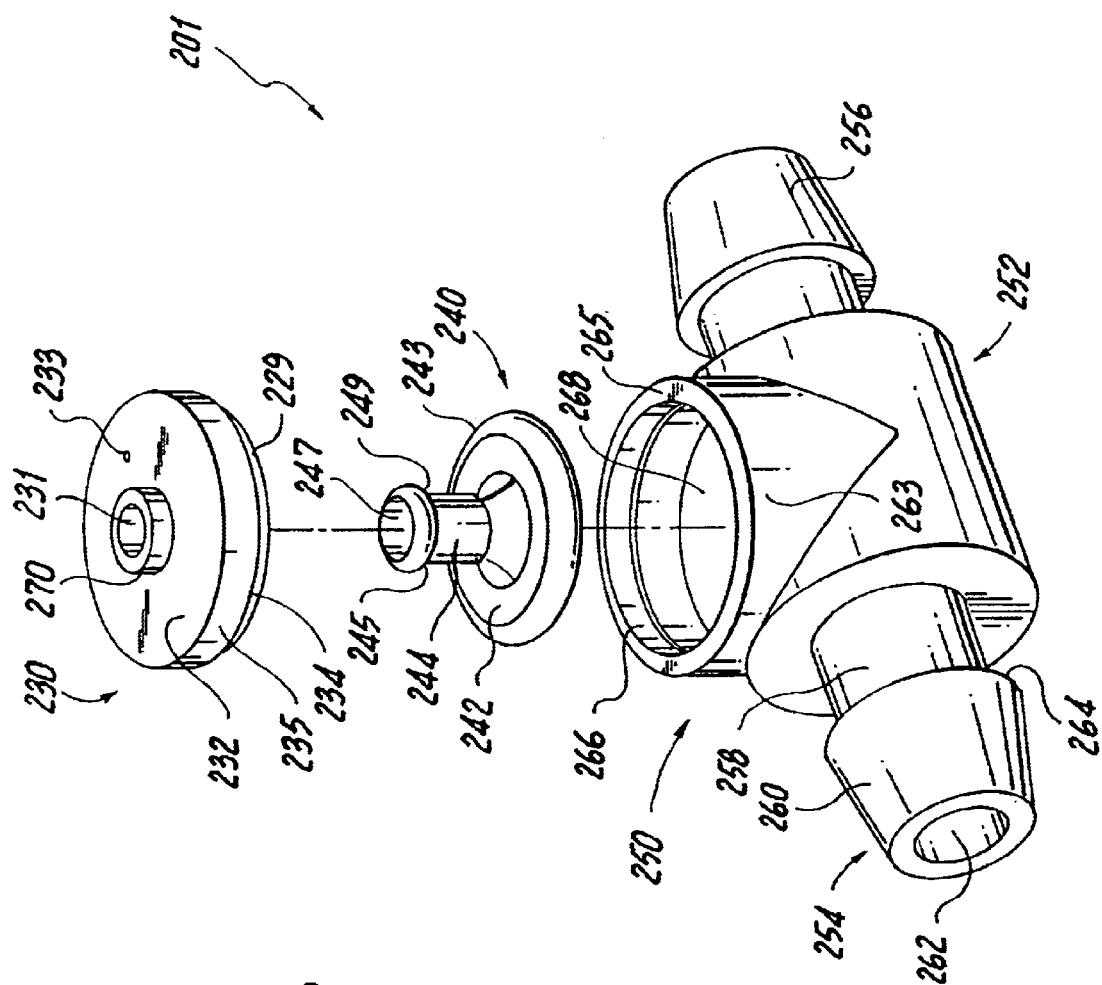
FIG. 8 is an exploded, perspective view of the valve assembly of FIG. 7.

As best shown in FIG. 7, in this embodiment of the present invention, the outlet tube 210 is divided into two sections, namely a first section 216 and a second section 218. The first section 216 is designed to attach to one portion of the valve assembly 201 and the second section 218 is designed to attach to another portion of the valve assembly 201. The connector 212 is preferably permanently connected to a first end 215 of the first section 216 of the outlet tubing 210. It will be appreciated that the length of the first section 216 will vary depending upon the precise application. Thus, when the connector 212 is releasably connected to the outflow port of the endoscope or other device, fluid will flow through an interior lumen of the connector 212 and into the length of the first section 216. Preferably, the valve assembly 201 is positioned approximately 6 inches from the outflow port of the endoscope (e.g., the first section 216 has a length of about 6 inches).

A second end 217 of the first section 216 is connected to the valve assembly 201. FIG. 7 illustrates the valve assembly 201 in an exploded perspective view. The valve assembly 201 is generally referred to as a one way control valve assembly which permits fluid to flow only in a single direction. Referring to FIGS. 7–11, the valve assembly 291 includes a cap 230, a valve member 240, and a valve housing 250. The valve housing 250 has a central body portion 252 with first and second connector legs 254, 256 extending therefrom. Preferably, the first and second connector legs 254, 256 are mirror images of one another. The first connector leg 254 is designed to mate with the second end 217 of the first section 216 of the outlet tube 210 and accordingly, has a complementary shape so that the second end 217 receives the first connector leg 254 in a sealed manner.

The first connector leg 254 of the exemplary embodiment has a first section 258 which extends from the central body portion 252 and a second section 260 which mates with the second end 217. A bore 262 is formed through the first and second sections 258, 260 and is preferably of the same diameter in both sections 258, 260. The bore 262 acts as a fluid conduit for carrying fluid through the outlet tube 210 and the valve assembly 201. Therefore, the bore 262 should have a diameter which is preferably approximately equal to the inner diameter of the first section 216. The second section 260 has a slight inward taper in a direction away from the first section 258. In other words, an outermost portion of the second section 260 has an outer diameter which is less than the diameter of the portion of the second section 260 which abuts the first section 258. Preferably, the first and second sections 258, 260 are integral to one another and more specifically, the valve housing 250 is preferably a single integrally formed member.

An annular shoulder 264 is formed between the first and second sections 258, 260 due to the differences in the outer diameters of the first and second sections 258, 260. The varying outer diameter of the second section 260 facilitates the seal between the first section 216 and the first connector leg 254 as the first section 216 is frictionally fit and pushed over the second section 260. Because the second connector leg 256 is a mirror image of the first connector leg 254, the second connector leg 256 will not be described in detail. Instead like elements have been numbered alike.

Figure 9:
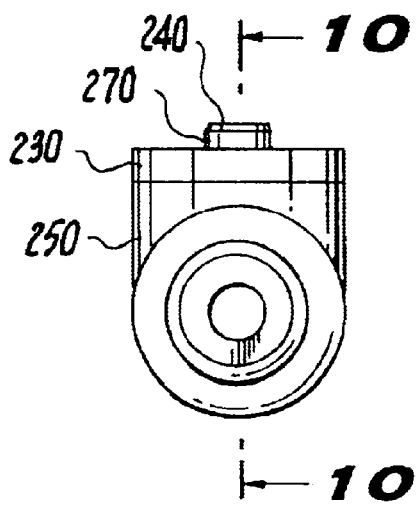
FIG. 9 is an end view of the valve assembly of FIG. 8.
Figure 10:
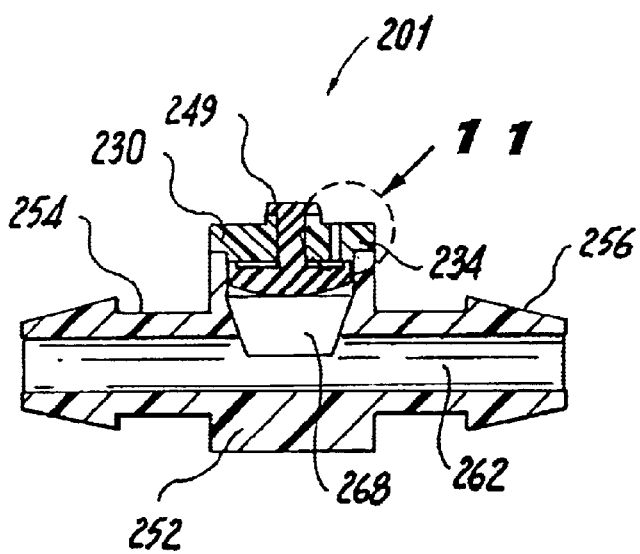
FIG. 10 is a cross-sectional side view of valve assembly taken along the line 10—10 of FIG. 9.

The central body portion 252 includes an upper portion 263 which has a cap opening 266 formed therein for receiving the cap 230 in a sealed manner. The cap opening 266 therefore has a complementary shape relative to the cap 230 and in the illustrated embodiment, the cap opening 266 is circular in shape. The upper portion 263 has a peripheral rim surface 265 which defines the cap opening 266 and also provides a surface for the cap 230 to seat against when the valve assembly 201 is completely assembled as shown in FIGS. 9–10.

The central body portion 252 also defines a compartment 268 which communicates with the bore 262 which extends through the central body portion 252. The bore 262 thus preferably has the same diameter through the valve housing 250 with the exception that the bore 262 opens into the compartment 268 which extends from the bore 262 to the cap opening 266. The compartment 268 is preferably a generally annular compartment designed to receive the valve member 240 and a portion of the cap 230.

As shown in FIGS. 7–11, the valve member 240 is of a type commonly used in one way control valve assemblies. The valve member 240 includes a deformable body 242 with a stem 244 extending outwardly therefrom. The deformable body 242 has a complementary shape as the compartment 268 and is designed to provide a hermetic seal between the compartment 268 and atmosphere when the valve member 240 is in a closed position. In the exemplary embodiment, the valve body 242 is an annular member having a peripheral outer edge 243. The stem 244 extends upwardly away from a center section of the body 242 with one end 245 having a disk-like member 247 formed thereat. The stem 244 is generally annular in nature and the disk-like member 247 has a diameter which is greater than the portion of the stem 244 which abuts the disk-like member 247. Thus, an annular shoulder 249 is formed by the disk-like member 247. Any number of suitable types of one way valve members 240 are commercially available and are typically formed at least in part of a thermoplastic material which permits the body 242 to deform when a predetermined pressure is applied thereto.

The cap 230 is hermetically sealed to the valve housing 250. The cap 230 has a first surface 229 and an opposing second surface 232 with the first surface 229 facing the housing 250 and the second surface 232 facing thereaway. In the exemplary embodiment, the cap 230 is annular in shape and includes an annular platform 234 which defines the first surface 229. The annular platform 234 is the portion of the cap 230 which is received within the cap opening 266 and provides the hermetic seal between the cap 230 and the housing 250. The annular platform 234 thus has a diameter which is preferably equal to the diameter of the cap opening 266. The cap 230 has a base portion 235 from which the annular platform 234 extends. The base portion 235 is also annular in shape and has a diameter which is greater than the diameter of the annular platform 234 so that the annular platform 234 forms a peripheral surface which seats against an inner surface of the housing 250. The base portion 235 thus seats against the peripheral rim surface 265 of the housing 250 to hermetically seal the compartment 268.

The cap 230 has a first opening 231 formed therein for receiving the stem 244 of the valve member 240. The first opening 231 is preferably formed in the center portion of the cap 230 and has a diameter which is preferably equal to the diameter of the portion of the stem 244 beneath the disk-like member 247 so that the stem 244 may be fitted through the first opening 231 as best shown in FIG. 9. The cap 230 also includes a spacer member 270 which is formed on the second surface 232. The spacer member 270 is preferably in the shape of a ring which surrounds the first opening 231. The spacer member 270 has a predetermined height which is the distance from the top edge of the spacer member 270 to the second surface 232. The disk-like member 247 of the valve member 240 seats against the spacer member 270 when assembled.

Figure 11:
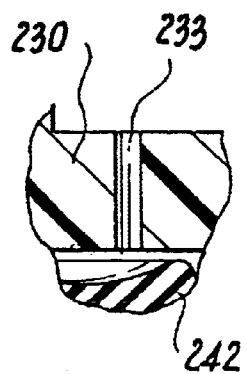
FIG. 11 is an exploded view of a portion of the valve assembly of FIG. 10.

The cap 230 also has a second opening 233 formed therein. The second opening 233 is a bleed thru hole which serves as a vent to atmosphere when the valve member 240 is in an open position, as will be described in greater detail hereinafter. The second opening 233 is preferably significantly smaller than the first opening 231. As best shown in FIGS. 10 and 11, the second opening 233 is in fluid communication with the compartment 268 and more specifically permits atmospheric air to fluidly communicate with the compartment 268 when the valve member 240 is open. Because the valve assembly 201 is of a one way control valve type, air (atmospheric pressure) may flow into the compartment 268 through the second opening 233; however, fluid is prevented from flowing out of (egressing) the valve assembly.

A second end 219 of the second section 218 of the outlet tube 210 is connected to the second connector leg 256 in the same manner that the second end 217 of the first section 216 is connected to the first connector leg 254. A first end 221 of the second section 218 is attached to the connector 214 which is used to connect the outlet tube 210 to the suction canister or other device. The length of the second section 218 may vary depending upon the precise application.

The operation of the valve assembly 201 will now be described. The valve assembly 201 acts as a one way control valve which only permits atmosphere pressure to enter, while preventing fluid from egressing out of the system. The valve assembly 201 opens and closes based upon a pressure difference being observed across the valve assembly 201. According to the present invention, the valve assembly 201 may be designed such that the valve member 240 is normally biased in an open position such that atmospheric air is introduced into compartment 268 under select conditions or the valve member 240 may be normally biased in a closed position such that it opens under other select conditions.

In the first embodiment when the valve member 240 is biased in an open position, the pressure acting on the valve member 240 before the suction source is actuated is equal to the pressure within the compartment 268. In other words, when no negative pressure is present in the outlet tube 210 because the suction source has not yet been actuated, the pressure acting on the valve member 240 in opposing directions is atmospheric pressure and thus the valve member 240 will remain in the open position. When the suction source is actuated, negative pressure is formed within the outlet tube 210 and this negative pressure causes the deformable body 242 to be drawn downward into the compartment 268. This results in the valve member 240 being maintained in the open position. As the negative pressure within the outlet tube 210 increases, the deformable body 242 will be further pulled downward resulting in the progressive opening of the valve member 240. In contrast, the valve member 240 closes when a positive pressure build-up results in the outlet tube 210. A positive internal pressure condition within the outlet tube 210 may result because of a number of reasons including (1) fluid build-up within the outlet tube 210 because one or more of the outlet tube 210, the suction canister, and other related equipment has become clogged and (2) the fluid is being pumped to the operative space at a much higher rate than the fluid is being withdrawn from the operative space by the suction source/suction canister.

In the closed position, the deformable body 242 seals the second opening 233 due to pressure being exerted on the deformable body 242 in a direction toward the cap 230. In other words, the pressure within the compartment 268 exceeds atmospheric pressure and causes the deformable body 242 to be moved upward against the cap 230. This effectively prevents atmospheric air flow into the compartment 268 through the second opening 233.

As previously mentioned, a pump (not shown) creates positive pressure in an inlet tube (not shown) and the operative site by directing fluid through the inlet tube to the operative site. As fluid is pumped to the surgical site, the flow rate of the fluid to the surgical site and through the inlet tube creates a positive pressure condition at the operative site (causing distention thereof). The suction source/canister acts to draw the fluid through the outlet tube 210 and the valve assembly 201 and thus serves to counter the positive pressure created by the pumping of the fluid to the operative site. Thus, the suction source/canister applies a negative internal pressure to outlet tube 210 to draw the fluid into and through the outlet tube 210. Alternatively, if the fluid flows by gravity from the operative site through the outlet tube 210, a negative internal pressure will also result because of a siphon effect which is caused by a vertical length of fluid within the outlet tube 210. As the suction canister becomes more and more full of fluid, the negative internal pressure begins to decrease within the outlet tube 210. In other words, the flow rate of pumped fluid (pump capacity) may become greater than the suction flow rate (suction capacity) at the suction canister resulting in a positive pressure increase at the operative site.

Due to the design of the valve assembly 201, the valve member 240 will close when the fluid pressure of the fluid flowing through the outlet tube 210 is greater than atmospheric pressure. Thus, when a positive pressure condition exceeding atmospheric pressure exists within the outlet tube 210, the valve member 240 will close. Atmospheric pressure is exerted on the valve member 240 through the second opening 233. As the positive pressure within the compartment 268 becomes greater, the valve member 240 will close more and more until the valve member 240 is fully closed.

Advantageously, the valve assembly 201 will remain open when a negative internal pressure condition exists within the valve assembly 201 or when pressure within the compartment 268 is less than atmospheric pressure. When a negative internal pressure exists within the outlet tube 210, the valve member 240 opens because the existence of negative internal pressure serves to draw the valve member 240 to its open position as a result of the suction forces applied by the suction canister.

This condition results when the suction capacity is greater than the pump capacity. In other words, the suction canister is drawing the fluid at a greater flow rate than the fluid is being pumped to the surgical site. The existence of excessive negative pressure is not desirable since this causes a loss in the distention at the surgical site.

When negative internal pressure exists within the outlet tube 210, the body 242 of the valve member 240 remain deformed away from the cap 230 to permit air to flow through the second opening 233 into the compartment 268. The peripheral outer edge 243 slightly "curls" downward when the fluid pressure within the outlet tube 210 is less than atmospheric pressure. In other words, the negative internal pressure draws the peripheral outer edge 243 downward. When there is even a slight deformation of the body 242, air flows around the body 242, more specifically the peripheral outer edge 243 thereof, and into the compartment 268. The compartment 268 is thus vented to atmospheric pressure.

By venting the compartment 268 to atmospheric pressure, the negative internal pressure is reduced. This causes a reduction in the suction level applied to the surgical site. The vent assembly 201 thus also acts as an anti-siphon device which breaks the vacuum created by the suction canister. The vent assembly 201 normally remains in the open position as long as the fluid pressure in the outflow tube 210 is less than atmospheric pressure. Once the positive fluid pressure within the outflow tube 210 becomes greater than atmospheric pressure, the valve assembly 200 will close and the deformable valve body 242 will seal the second opening 233. Because the valve assembly 200 is a one way control valve, the fluid is prevented from egressing from the valve assembly 200 and furthermore if a build-up of fluid occurs in the outlet tube 210 due to the suction canister becoming more and more filled, the valve member 240 closes and thus, fluid will be prevented from egressing from the system under such circumstances.

In this embodiment, the valve assembly 200 is designed so it is normally biased open and it closes when a positive pressure within the compartment 268 exceeds atmospheric pressure causing the deformable valve body 242 to seal against the cap 230.

In another embodiment, the valve assembly 201 is set to a predetermined cracking pressure. As is know, the cracking pressure of a valve is the pressure at which the valve assembly 201 bleeds atmosphere into the system. In some surgical procedures, it is desirable to tune the valve assembly 201 so that it does not open upon the observance of a negative pressure increase or a positive pressure decrease, but rather the valve assembly 201 is pre-loaded so that the valve assembly 201 opens only when a substantial negative pressure increase is observed or a substantial pressure decrease is observed. For example, in some orthopedic procedures, the physician prefers to perform the procedure at a predetermined pressure rate, e.g., a pressure of about 100 mil of mercury, so that a higher suction rate occurs at the surgical site, i.e. at the knee. Thus, the valve assembly 201 should be set to have a cracking pressure of about 100 mil of mercury before the vent assembly 201 opens.

In this embodiment when the valve assembly 201 is preloaded, the valve member 240 is normally biased closed. The valve member 240 will remain closed until the pressure exerted on the valve member 240 exceeds the set point (cracking point) of the valve assembly 201 resulting in the deformation of the valve body 242 to permit atmospheric air to enter the compartment 268.

As is known in the art, the pre-loading of a valve assembly, e.g., valve assembly 201, is a mechanical operation in which the valve assembly is tuned to a specific cracking point. At pressures less than the pre-loaded cracking pressure, the valve assembly 201 remains closed. One manner of pre-loading the valve assembly 201 is to apply a greater force on the valve body 242 so that so that a pressure greater than a predetermined pressure is required to cause the deformation of the valve body 242 and bleeding of the system. One technique for applying a greater force on the valve body 242 is to increase the height of the spacer member 270. When the stem 244 is assembled to the cap 230 by pushing the stem 244, including the disk-like member 247, through the first opening 231 formed in the cap 230, the disk-like member 247 still seats against the spacer member 270. However, the increase in height of the spacer member 270 causes the valve body 242 to be pulled with more force against the cap 230 because the valve member 240 has not been modified. The result is that a greater force is exerted on the valve member 240 in a direction toward the cap 230 and therefore a greater opposite force is required to deform the valve body 242 to cause the opening of the valve assembly 201. In other words, the valve body 240 deforms either when a substantial increase in negative internal pressure is observed or a substantial decrease in the positive internal pressure is observed such that the pressure acting on the valve body 242 exceeds the pre-load value of the valve assembly 201.

In this embodiment, the valve assembly 201 is tunable so that it has a certain cracking pressure. For example, if a greater cracking pressure is desired, the height of the spacer member 270 may be increased so that a greater force is exerted on the valve body 242. Likewise, if a decrease in cracking pressure is desired, the height of the spacer member 270 may be reduced. It will be understood that it is within the scope of the present invention that other methods of pre-loading the valve assembly 201 may be used to set the cracking pressure of the valve assembly 201 to a predetermined pressure. Because the valve assembly 201 has a simple design and is relatively inexpensive to produce, valve assemblies 201 may be easily interchanged with the outlet tube 210 so that a specific type of valve assembly 201 may be used for a given application.

In yet another embodiment of the present invention, the second opening 233 of the valve member 240 may be selectively opened or closed by manipulating a slide member 280 or the like. The slide member 280 may comprise any number of types of members and broadly is a member which may be moved so as to variably close the second opening 233. In other words, the second opening 233 is selectively sealed by positioning the slide member 280 thereof. This permits the user to selectively control the fluid flow path of air into the compartment 268. In other words, the user controls whether the compartment 268 is vented to atmospheric pressure. For example, as the slide member 280 is manipulated so as to close the second opening 233, the venting to atmospheric conditions is reduced.

As the second opening 233 is closed, the negative internal pressure within the outlet tube 210 is permitted to increase. As previously mentioned, excessive negative internal pressure is not desirable because it results in loss of distention at the surgical site. If the user notices that a loss of distention is occurring, the user needs only to move the slide member 280 so as to open the second opening 233. This permits more atmospheric venting to occur. As the second opening 233 is opened to a greater degree, a reduction in the negative internal pressure is observed within the outlet tube 210. In other words, there is an increase in the positive internal pressure within the outlet tube 210. If the positive internal pressure becomes too great (i.e., insufficient negative internal pressure), the user simply adjusts the slide member 280 to cause partial or complete closing of the second opening 233.

It will be appreciated by one of skill in the art that the slide member 180 may comprise a stopcock, a slide switch, or any other type of mechanism that permits the user to selectively open and close the second opening 233. Alternatively, the user may use one of his/her fingers to partially or completely cover the second opening 233. For example, if the second opening 233 is completely open and the user notices that the positive internal pressure is becoming too great, as evidenced by excessive distention, the user simply needs to place a finger over a selected portion of the second opening 233 until the distention decreases to a desired level. If the user's finger position on the second opening 233 causes too great of an increase in the negative internal pressure within the outlet tube 210, the user simply readjusts the finger position to cause an increase in atmospheric venting through the second opening 233.

Figure 12:
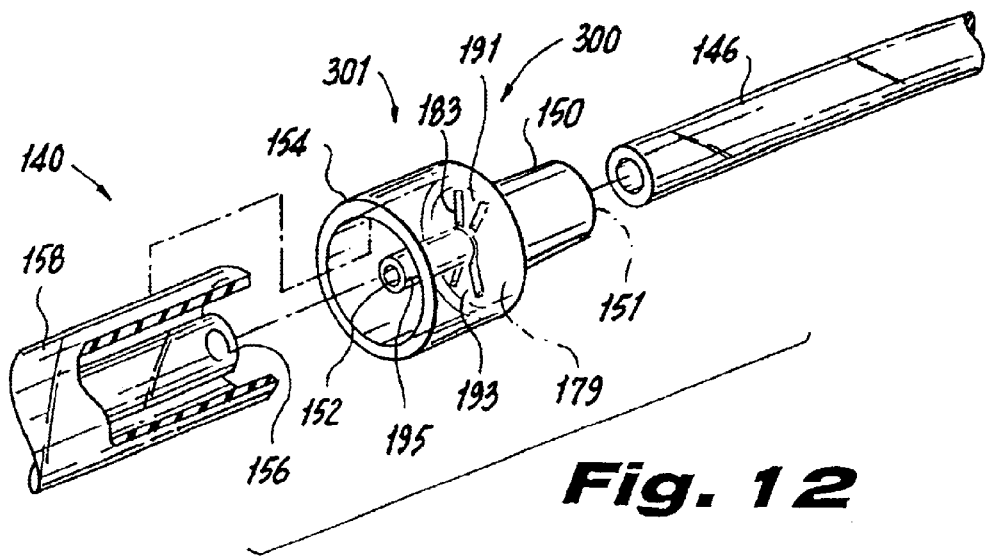
FIG. 12 is an exploded, perspective view of an anti-siphon adapter and tubing for use with the fluid management assembly of FIG. 2.
Figure 13:
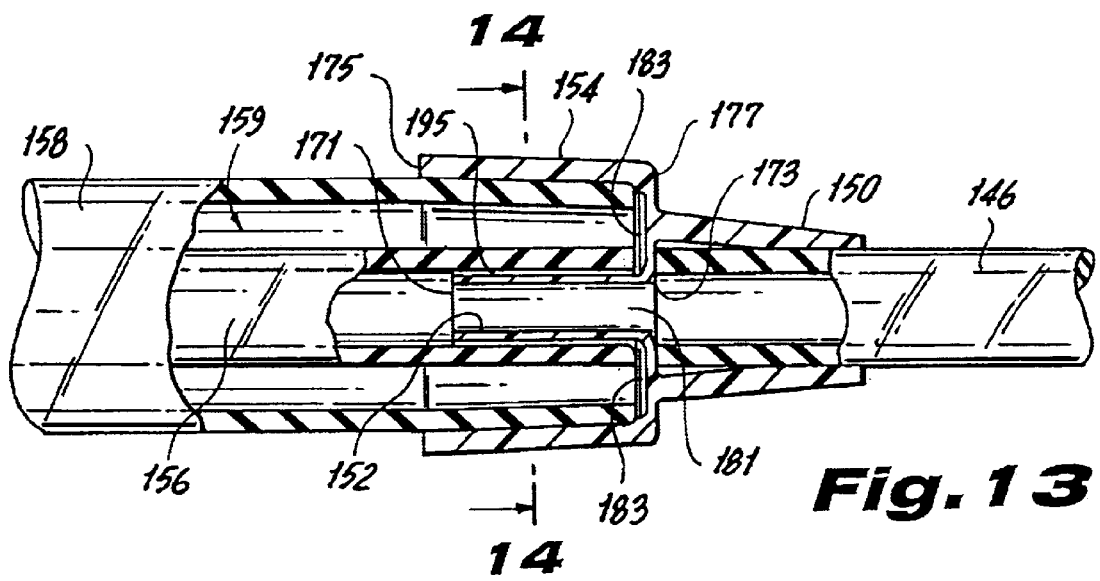
FIG. 13 is a cross-sectional side view of a portion of the outlet tube and adapter of FIG. 12.
Figure 14:
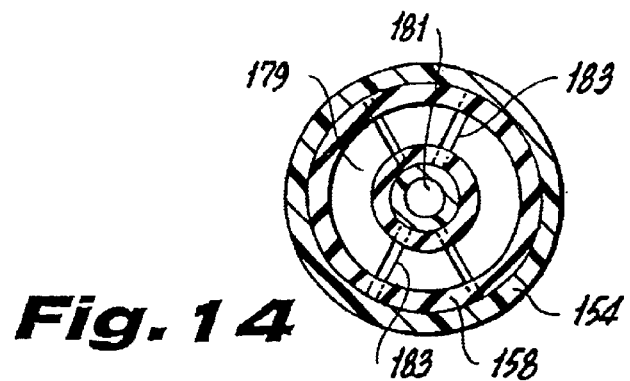
FIG. 14 is a cross-sectional view taken along the line 14—14 of FIG. 13.

Referring now to FIGS. 12–14, another embodiment of the present invention is provided. In this embodiment, another adapter member 300 is presented for use with the outlet tube 140 and is intended to take the place of the adapter member 148 shown in FIG. 5. The outlet tube 140 thus includes the connectors 142, 144 (FIG. 4) and is intended to be used in the fluid management system 40, shown in FIGS. 2–3, and replace the outflow tubing 91 thereof. In other words, the adapter member 300 may act as the atmospheric vent 200 described with reference to FIGS. 2–3.

The adapter member 300 includes the nipple region 150 telescopically extended over the length of tubing 146 for retaining the tubing 146 within the adapter member 300. The nipple region 150 defines the interior cavity 151 which receives the tubing 146 and aligns the tubing 146 with the tube segment 156 so that fluid flows from the tubing 146 into the tube segment 156.

The adapter member 300 also includes a second section 301 which is preferably integrally formed with the nipple region 150. The second section 301 is formed of a pair of coaxial, generally tubular members 152, 154. More specifically, the outer tubular member 154 has a first diameter and the inner tubular member 152 has a second diameter with the first diameter being greater than the second diameter. The inner tubular member 152 has a first end 171 and a second end 173 and has a bore extending therethrough so that it is open at both ends 171, 173. The outer tubular member 154 has a first end 175 and a second end 177 with the nipple region 150 extending from the second end 177. The first end 175 is an open end, while the second end 177 is only partially open.

More specifically, the second end 177 of the outer tubular member 154 is closed by an annular wall 179. The annular wall 179 has an opening 181 formed therein and the inner tubular member 152 seats against the annular wall 179 and is preferably integrally formed therewith. Preferably, the inner tubular member 152 has a length which is less than the length of the outer tubular member 154. The opening 181 is axially aligned with the bore of the inner tubular member 152. The opening 181 is in communication with and opens into the cavity 151 so that fluid may flow from the cavity 151 through the opening 181 and into the bore formed in the inner tubular member 152. The annular wall 179 has a first surface which faces the inner tubular member 152 and a second surface which faces the nipple region 150. When the tubing 146 is disposed within the cavity 151 of the nipple region 150, the tubing 146 preferably seats against or is in close proximity to the second surface of the annular wall 179. The nipple region 150 is configured so that when the tubing 146 is fully inserted against or in close proximity to the second surface of the annular wall 179, the opening of the tubing 146 aligns with the opening 181.

The annular wall 179 also includes a plurality of spaced ribs 183 which are formed on and extend outwardly from the first surface of the annular wall 179. In one exemplary embodiment, each rib 183 is a rib having a longitudinal axis. The ribs 183 are formed on the annular wall 179 according to a select predetermined pattern. In the illustrated embodiment, the ribs 183 are radially spaced around the opening 181 and the second end 173 of the inner tubular member 152. The ribs 183 may or may not extend completely to the inner surface of the outer tubular member 154. Depending upon the application, the height of the ribs 183 may be varied. As shown in FIG. 12, in one embodiment, the ribs 183 are formed in two pairs of ribs 183 such that a gap 191 is formed between adjacent ribs 183 of one pair. An angle is formed between the ribs 183; however, the precise measurement of the angle defined between the ribs 183 is not critical to the practice of the present invention.

The inner tubular member 152 connects to the tube segment 156 which leads to the suction canister and includes-the connector 144 at the distal end thereof. The inner diameter of the tube segment 156 is equal to or slightly less than the outer diameter of the inner tubular member 152 so that a frictional, sealed fit results between the tube segment 156 and the inner tubular member 152. The tube segment 156 is directed into the second section around the inner tubular member 152 until one end of the tube segment 156 and the sleeve 158 seat against the ribs 183. The ribs 183 thus serves as spacers which prevent the tube segment 156 and the sleeve 158 from seating against the first surface of the annular wall 179. A space, generally indicated at 193, is formed between the ends of the tube segment 156 and the sleeve 158 and the first surface of the annular wall 179. The space 193 is approximately equal to the height of the ribs 183. The sleeve 158 and the tube segment 156 define the annular space 159 between the two. The outer diameter of the sleeve 158 is preferably equal to or slightly greater than the inner diameter of the outer tubular member 154 so that a sealed, frictional fit results between the sleeve 158 and the outer tubular member 154 when the sleeve 158 is inserted therein. The ribs 183 extend sufficiently along the first surface of the annular wall 179 so that at least a portion of the sleeve 158 seats against the ribs 183 when inserted into the outer tubular member 154.

According to the present invention, the inner tubular member 152 has a plurality of longitudinal grooves 195 formed therein. The longitudinal grooves 195 are formed in the inner tubular member 152 from the first end 171 to the second end 173. In the illustrated embodiment, there are two longitudinal grooves 195 which are preferably formed about 180° from one another. Each longitudinal groove 195 is orientated such that it is disposed within the gap 191 between the ribs 183. When the tube segment 156 is disposed over the inner tube member 152, the inner surface of the tube segment 156 seats against the outer surface of the inner tube member 152 and therefore the longitudinal grooves 195 serve as vent channels which permit air to flow through the longitudinal grooves 195 and into the tube segment 156. More specifically, the space 193 is in fluid communication with the annular space 159 and accordingly, the gaps 191 are also in fluid communication with the annular space 159. Because the longitudinal grooves 195 are in fluid communication with the gaps 191, the fluid, e.g., air, is permitted to flow through the annular space 159 and into the tube segment 156.

The operation of the adapter member 300 will now be described in greater detail. The adapter member 300 acts as an atmospheric vent and may be used in combination with the fluid management assembly 40 of FIGS. 2–3 or may be used in another type of fluid system such as that described in reference to FIG. 4, where the outlet tube 140 is connected to a suction canister or the like at one end and an endoscope at the other end.

During the endoscopic procedure, fluid is delivered, i.e., pumped, to the operative site by conventional means, e.g., the endoscope may or may not be used to perform such operation. The fluid is then removed from the operative site by any number of techniques depending upon the precise application. For example, a gravitational flow system may be used to remove the fluid; however, it is more common to employ some type of aspiration system to remove the fluid. The outlet tube 140 is thus typically connected to the suction canister which creates a negative internal pressure condition within the outlet tube 140 to draw the fluid from the operative site. As previously mentioned, maintaining the precise pressure level within the outlet tube 140 is important since it is desirable for the operative site not to become over-distended due to excessive positive pressure but also not to become under-distended due to excessive negative internal pressure.

If the system included no vent, then the suction canister may create an undesirable negative pressure condition within the outlet tube 140 by withdrawing the fluid at an excessive pressure, which leads to unwanted loss of distention at the operative site. The atmospheric vent 200 introduces air (atmospheric pressure) into the outlet tube 140 so that any vacuum that may have been formed in the outlet tube 140 is broken. The introduction of air into the outlet tube 140 increases the internal pressure within the outlet tube 140 and thus serves to counteract the negative internal pressure build-up caused by the suction canister and fluid flow.

More specifically, as fluid flows through the tubing 146 and into the inner member 152 and the tube segment 156, air is drawn through the space 159 toward the annular wall 179. An atmospheric vent path is provided and is defined by the space 159, the gaps 191 and the longitudinal grooves 195. Air flows through the space 159 and into the gaps 191 which are in fluid communication with the longitudinal grooves 195. The air then flows within the longitudinal grooves 195 and into the tube segment 156. This results in air being continuously introduced into the tube segment 156 and more specifically, air mixes with the fluid flowing therethrough to increase the internal positive pressure of the outlet tube 140. By introducing air into the tube segment 156 and relieving any excessive negative internal pressure build-ups, the operative site may be properly distended even when the pressure of the suction source, e.g., suction canister, is greater than the pressure of the device which pumps fluid to the operative site. For example, if fluid is pumped at a pressure of 100 psi and the suction canister is drawing the fluid from the operative site at a pressure of 200 psi, excessive negative pressure will result in the outlet tube 140. This will result in a loss of or lack of distention at the operative site due to the suction forces present in the outlet tube 140. The use of atmospheric vent 200 ensures that the vacuum created by the suction canister is broken by introducing atmospheric pressure into the outlet tube 140 and therefore, the operative site is properly distended.

It will also be appreciated that the tube segment 156 and the outer member 154 may be connected to either a drape for collection of any fluid or may be directly connected to a suction canister, as previously-mentioned. When the segment 156 and the member 154 are connected to the drape, negative pressure increases as the fluid blocks up along the length of the tube segment 156. As one of skill in the art understands, there is a relationship between the length of the tube segment 156 and the negative pressure. As the length of the tube segment 156 increases, the system imposes negative pressure which corresponds to the length of the tube segment 156 as the fluid is gravity fed through the tube segment 156 to the drape. The negative internal pressure will increase as the length of the tube increases due to the siphon effect caused by the vertical height of the fluid outflow from the endoscope. Thus, even when the outlet tube 140 is connected to a drape and a suction force is not applied, the atmospheric vent 200 advantageously ensures that an excessive negative internal pressure condition does not exist in the outlet tube 140.

Having thus described a preferred embodiment of the present invention, it is to be understood that the above described arrangement and system is merely illustrative of the principles of the present invention, and that other arrangements and systems may be devised by those skilled in the art without departing from the spirit and scope of the invention as claimed below.

What is claimed is:

1. A fluid management assembly for use in an endoscopic procedure, the assembly comprising:
    a first line defining a passage for the flow of fluid and having a length, the first line having a first end for connection to an endoscope and an opposing second end;
    a second line defining a passage for the flow of fluid and having a length, the second line having a first end for connection to a drape and an opposing second end;
    a Y-connector having first and second legs in fluid communication with the second ends of the first and second lines;
    a third line coupled at a first end to a third leg of the Y-connector, the third line having a second end for connection to a suction source, the third line having a predetermined length such that the Y-connector is positioned in close proximate relation to the suction source, the length of the third line being less than the length of each of the first and second lines; and
    an anti-siphon adapter disposed within the first line for introducing atmospheric pressure into the first line to reduce negative pressure within the first line, thereby substantially preventing a siphoning action from occurring within the first line.

2. An assembly according to claim 1, wherein the third line has a length of about 6 inches.

3. An assembly according to claim 1, wherein the lengths of the first and second lines are greater than about 10 feet.

4. An assembly according to claim 1, wherein the first line has a first section extending from the endoscope to the adapter and a second section extending from the adapter to the Y-connector, the adapter permitting fluid to flow from the first section to the second section.

5. An assembly according to claim 4, wherein the second section is formed of an inner tube and an outer tube, the inner tube carrying the fluid from the adapter to the Y-connector and the outer tube being open to atmosphere at an end opposite the adapter, wherein atmospheric pressure is introduced to the adapter by air flowing between the outer and inner tubes.

6. An assembly according to claim 1, wherein the adapter defines an atmospheric fluid path by which atmospheric air flows into the adapter and mixes within the fluid flowing within the first line from the endoscope, the introduction of atmospheric air into the fluid causing the negative pressure to be decreased, thereby substantially preventing the siphoning action from occurring within the first line.

7. A fluid management assembly for use in an endoscopic procedure, the assembly comprising:
    a first line defining a passage for the flow of fluid and having a length, the first line having a first end for connection to an endoscope and an opposing second end;
    a second line defining a passage for the flow of fluid and having a length, the second line having a first end for connection to a drape and an opposing second end;
    a Y-connector having first and second legs in fluid communication with the second ends of the first and second lines;
    a third line coupled at a first end to a third leg of the Y-connector, the third line having a second end for connection to a suction source, the third line having a predetermined length such that the Y-connector is positioned in close proximate relation to the suction source, the length of the third line being less than the length of the first and second lines; and an anti-siphon adapter disposed within the first line for introducing atmospheric pressure into the first line to reduce negative pressure within the first line, thereby substantially preventing a siphoning action from occurring within the first line, wherein the first and second lines are affixed along a first portion of the lengths thereof, the first and second lines being separated from one another at a first location and a second location.

8. An assembly according to claim 7, wherein a portion of the first line from the first location to the first end defines a scope leg and a portion of the second line from the first location to the first end defines a drape leg.

9. An assembly according to claim 8, wherein the scope leg is longer than the drape leg.

10. A fluid management assembly for use in an endoscopic procedure, the assembly comprising:

a first line defining a passage for the flow of fluid and having a length, the first line having a first end for connection to an endoscope and an opposing second end;

a second line defining a passage for the flow of fluid and having a length, the second line having a first end for connection to a drape and an opposing second end;

a Y-connector having first and second legs in fluid communication with the second ends of the first and second lines;

a third line coupled at a first end to a third leg of the Y-connector, the third line having a second end for connection to a suction source, the third line having a predetermined length such that the Y-connector is positioned in close proximate relation to the suction source, the length of the third line being less than the length of each of the first and second lines; and an adjustable atmospheric vent disposed within the first line for introducing atmospheric pressure into the first line, the atmospheric vent opening and closing in response to pressure changes within the first line.

11. An assembly according to claim 10, wherein the atmospheric vent is biased open under normal operating conditions when the pressure within the first line is less than atmospheric pressure, the introduction of atmospheric pressure into the first line creating an anti-siphon effect by increasing the pressure within the first line to substantially prevent a siphoning action from occurring within the first line.

12. An assembly according to claim 11, wherein the atmospheric vent closes when pressure within the first line exceeds a predetermined value.

13. An assembly according to claim 12, wherein the predetermined value is atmospheric pressure.

14. An assembly according to claim 10, wherein the atmospheric vent is disposed proximate to an outflow connection of the endoscope.

15. An assembly according to claim 10, wherein the atmospheric vent comprises a one way control valve.

16. An assembly according to claim 10, wherein the atmospheric vent includes a valve body having a valve member disposed therein and a vent opening for permitting atmospheric air to enter the first line, the valve member being positionable between an open position in which atmospheric air enters through the vent opening and a closed position in which the valve member closes the vent opening.

17. An assembly according to claim 16, wherein the valve member closes when the internal pressure exceeds atmospheric pressure.

18. An assembly according to claim 16, wherein the valve member comprises a deformable member which deforms when internal pressure within the first line exceeds atmospheric pressure, the deformation of the valve member preventing atmospheric air from flowing through the vent opening and communicating with the fluid flowing through the first line.

19. An assembly according to claim 10, wherein the atmospheric vent is biased closed under normal operating conditions when the pressure within the first line is less than a predetermined value, the atmospheric vent opening when the pressure within the first line exceeds the predetermined value causing the introduction of atmospheric pressure into the first line to create an anti-siphon effect by increasing the pressure within the first line to substantially prevent a siphoning action from occurring within the first line.

20. An assembly according to claim 19, wherein the atmospheric vent is pre-loaded and has an associated set pressure cracking point, the atmospheric vent opening when the internal pressure within the first line exceeds the cracking point.

21. An assembly according to claim 20, wherein the atmospheric vent includes a valve body having a valve member disposed therein and a vent opening for permitting atmospheric air to enter the first line, wherein the set pressure cracking point is a predetermined negative pressure, the atmospheric vent opening when the internal negative pressure within the first line exceeds the cracking point of the valve member.

22. An assembly according to claim 21, wherein the valve member comprises a deformable member which deforms when internal negative pressure within the first line exceeds the cracking point of the valve member, the deformation of the valve member permitting atmospheric air to flow through the vent opening and communicate with the fluid flowing through the first line resulting in a decrease in the negative pressure within the first line.

23. An assembly according to claim 10, wherein the atmospheric vent is disposed about 6 inches from an outflow connection of the endoscope.

24. A fluid management assembly for use in an endoscopic procedure performed at an operative site, the assembly comprising:

a first line defining a passage for the flow of fluid from the operative site after the fluid has been delivered to the operative site at a first pressure, the first line having a first end for connection to an endoscope and an opposing second end for connection to one of a suction canister and a drape, the fluid flowing within the first line from the operative site at a second pressure; and an adjustable atmospheric vent disposed within the first line for introducing atmospheric pressure into the first line to decrease internal pressure within the first line when the second pressure exceeds the first pressure by a predetermined amount, the atmospheric vent having a deformable valve body and a valve member coupled to the valve body, the valve member having a bleed hole formed therein and open to atmosphere, wherein the atmospheric vent is pre-loaded so that the atmospheric pressure is introduced into the first line when the second pressure exceeds a set pressure cracking point of the atmospheric vent such that the valve body deforms resulting in the bleed hole being opened.

25. An assembly according to claim 24, wherein the atmospheric pressure is introduced when the second pressure is greater than the first pressure.

26. An assembly according to claim 24, wherein the second pressure is a negative pressure generated by operation of a suction source associated with the suction canister.

27. An assembly according to claim 24, wherein the atmospheric vent is a one way control valve.

28. A method of managing patient fluid, the method comprising:

providing a fluid management assembly comprising a first line defining a passage of fluid from an operative site after the fluid has been delivered to the operative site at a first pressure, the fluid flowing from the operative site at a second pressure, wherein the first line has a first section and a second section;

attaching an endoscope to a first end of the first line;

connecting one of a suction source and a drape to a second end of the first line;

disposing an anti-siphon adapter within the first line such that the first section thereof extends from the endoscope to the adapter and the second section extends from the adapter to a connector at the second end of the first line, wherein the second section is formed of an inner tube and an outer tube, the inner tube carrying the fluid from the adapter to the connector and the outer tube being open to atmosphere at an end opposite the adapter; and introducing atmospheric pressure into the first line by air flowing between the outer and inner tubes to reduce any negative pressure within the first line, thereby substantially preventing a siphoning action from occurring within the first line.

29. A method according to claim 28, wherein the atmospheric vent is disposed proximate to the endoscope so that the introduction of atmospheric pressure into the first line increases the pressure at an outflow connector of the endoscope.

30. A method of managing patient fluid, the method comprising:

providing a fluid management assembly comprising first, second, and third lines, the first line defining a passage for the flow of fluid from an operative site after the fluid has been delivered to the operative site at a first pressure, the fluid flowing from the operative site at a second pressure, the third line having a length that is less than a length of each of the first and second lines;

attaching an endoscope to a first end of the first line;

attaching a second end of the first line to an input port of a Y-connector;

attaching a drape to a first end of the second line, with a second end of the second line being attached to another input port of the Y-connector;

attaching one end of the third line to an outlet port of the Y-connector and another end of the third line being attached to a suction source;

disposing an atmospheric vent within the first line; and introducing atmospheric pressure into the first line when internal pressure within the first line is less than a predetermined pressure and in the case that the internal pressure is greater than the predetermined pressure, the method further including closing the atmospheric vent.

31. A method according to claim 30, wherein the predetermined pressure is atmospheric pressure.

32. A method of managing patient fluid, the method comprising:

providing a fluid management assembly comprising a first line defining a passage for the flow of fluid from an operative site after the fluid has been delivered to the operative site at a first pressure, the fluid flowing from the operative site at a second pressure;

attaching an endoscope to a first end of the first line;

connecting one of a suction source and a drape to a second end of the first line;

disposing an atmospheric vent within the first line, the atmospheric vent having a deformable valve body and a valve member coupled to the valve body, the valve member having a bleed hole formed therein which is open to atmosphere;

pre-loading the valve body so that the atmospheric vent has an associated set pressure cracking point; and opening the atmospheric vent to introduce atmospheric pressure into the first line when the internal pressure within the first line exceeds the cracking point resulting in the valve body deforming relative to the valve member and opening the bleed hole.

33. A method according to claim 32, wherein the atmospheric vent remains open so long as the internal pressure within the first line exceeds the cracking point, the cracking point being a pressure less than atmospheric pressure.

34. A method according to claim 32, further including:

closing the atmospheric vent when the internal pressure within the first line is less than the cracking point.

* * * * *